(12) United States Patent  
Tsuyuki et al.

(10) Patent No.: US 8,761,339 B2  
(45) Date of Patent: Jun. 24, 2014

(54) METHOD AND APPARATUS FOR IMAGE DIAGNOSIS

(75) Inventors: Masaharu Tsuyuki, Tochigi-ken (JP); Hiroki Taguchi, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 562 days.

(21) Appl. No.: 13/016,307

(22) Filed: Jan. 28, 2011

(65) Prior Publication Data

US 2011/0194675 A1  Aug. 11, 2011

(30) Foreign Application Priority Data

Jan. 29, 2010 (JP) ............................... P2010-019199  
Jan. 27, 2011 (JP) ................................ P2011-15810

(51) Int. Cl.  
*H05G 1/64* (2006.01)  
*G06K 9/20* (2006.01)

(52) U.S. Cl.  
USPC ........................... 378/95; 378/98.12; 382/131

(58) Field of Classification Search  
USPC ............... 378/4–20, 91, 98, 98.8, 98.12, 204, 378/210, 901; 382/128, 130–132, 168–172, 382/190–194, 206

See application file for complete search history.

(56) References Cited

U.S. PATENT DOCUMENTS 6,876,720 B2 * 4/2005 Tsuyuki ............................ 378/8

FOREIGN PATENT DOCUMENTS

JP  2002-233525  8/2002

\* cited by examiner

*Primary Examiner* — Anastasia Midkiff  
(74) *Attorney, Agent, or Firm* — Oblon, Spivak, McClelland, Maier & Neustadt, L.L.P.

(57) ABSTRACT

An image diagnostic apparatus including a scan unit to repeatedly scan a subject to repeatedly acquire acquisition data related to the subject, a generation unit to generate medical images related to the subject based on the acquired acquisition data, a monitoring unit to monitor a change in the medical images based on a specified pixel value band having an upper limit and a lower limit, a controller unit to control timing of a predetermined action of the scan unit based on of the change in the medical images monitored by the monitor unit, wherein the predetermined action of the scan unit is at least one of changing a scan condition, stopping a scan, and outputting guidance to the subject.

22 Claims, 10 Drawing Sheets

METHOD AND APPARATUS FOR IMAGE DIAGNOSIS

CROSS-REFERENCE TO RELATED APPLICATIONS

This application is based upon and claims the benefit of priority from Japanese Patent Application No. 2010-19199, filed Jan. 29, 2010, and Japanese Patent Application No. 2011-15810, filed Jan. 27, 2011, the entire contents of which are incorporated herein by reference.

FIELD

Embodiments described herein relate generally to a method and an apparatus for image diagnosis of an object in which contrast medium has been injected.

BACKGROUND

An imaging diagnostic apparatus such as an X-ray computed tomography imaging apparatus scans a subject and generates medical image data. Contrast medium is often injected into the subject for image diagnosis of the subject's blood vessels. For example, an X-ray computed tomography imaging apparatus is used to describe blood vessels in CT images by scanning the subject in which contrast medium has been injected using X-rays.

In one application of the scan using a contrast medium and an X-ray computed tomography imaging apparatus, there is a developed function that monitors the degree of enhancement (e.g., the average CT value, etc.) in a region of interest (ROI) of a CT image. The function makes the apparatus execute a transition from a monitoring scan to a main scan according to the degree of enhancement. For example, the ROI is set in a region of a blood vessel on a CT image. The ROI is fixed on the CT image. Therefore, if the subject's body or organs move, the monitored region of the blood vessel might move to an area different from the ROI. In this case, the main scan might start at an incorrect time or might not start at all.

DETAILED DESCRIPTION

In one embodiment, there is provided an image diagnostic apparatus includes a scan unit configured to repeatedly scan a subject and to repeatedly acquire acquisition data related to the subject, the generation unit configured to generate medical images related to the subject based on the acquired acquisition data, a monitoring unit configured to monitor a change in the medical images based on a specified pixel value band, which has an upper limit and a lower limit, a controller unit configured to control timing of a predetermined action of the scan unit based on the change in the medical images monitored by the monitoring unit, wherein the predetermined action of the scan unit is at least one of changing a scan condition, stopping a scan, and outputting guidance to the subject.

In another embodiment, the monitoring unit further includes a calculator configured to calculate an index by adding a plurality of pixel values in a selected subset of sub-ROIs selected from a plurality sub-ROIs; and a determination unit configured to determine whether or not the index reaches a predetermined threshold, wherein the controller is further configured to prohibit execution of the predetermined action when the index does not reach the predetermined threshold, and to cause the predetermined action to be executed when the index reaches the predetermined threshold.

Hereinafter, an image diagnostic apparatus and method of a first embodiment is explained with reference to the drawings.

The image diagnostic apparatus of the first embodiment monitors a degree of enhancement and controls the timing of predetermined actions based on the degree of enhancement. Here, the predetermined actions may include a change of the scan conditions, stopping the scan, and the output of guidance for the subject, such as a respiration instruction. Therefore, the imaging diagnostic apparatus is adaptable to any modality in which scanning to determine contrast medium enhancement can be executed, such as an X-ray computed tomography imaging apparatus, a simple X-ray diagnostic apparatus, an ultrasound diagnostic apparatus, a magnetic resonance imaging apparatus, and a nuclear medicine diagnostic apparatus. However, hereinafter, for specialized explanation, a case in which the imaging diagnostic apparatus is an X-ray computed tomography imaging apparatus is explained.

There are various types of X-ray computed diagnostic apparatuses, such as the rotate/rotate type or the stationary/rotate type, etc. In the rotate/rotate type, an X-ray tube and an X-ray detector rotate as a unit. However, in the stationary/rotate type, many detector elements are circularly arranged and only an X-ray tube rotates around the subject. The first embodiment is adaptable to both types of the X-ray apparatuses. However, here, an example using the rotate/rotate type of X-ray apparatus is explained.

In addition, as a image reconstruction method used by the X-ray computed tomography imaging apparatus, there are a full-scan method and a half-scan method. In the full-scan method, projection data from all round the subject, which means approximately $2\pi$ [rad], is needed for reconstruction of one slice of the CT image. In the half-scan method, projection data of $\pi + \alpha$ [rad] ($\alpha$=the fan angle) is needed for reconstruction of one slice of the CT image. The first exemplary embodiment is adaptable to both types. However here, for specific explanation, the case in which the full-scan is use is explained.

Figure 1:
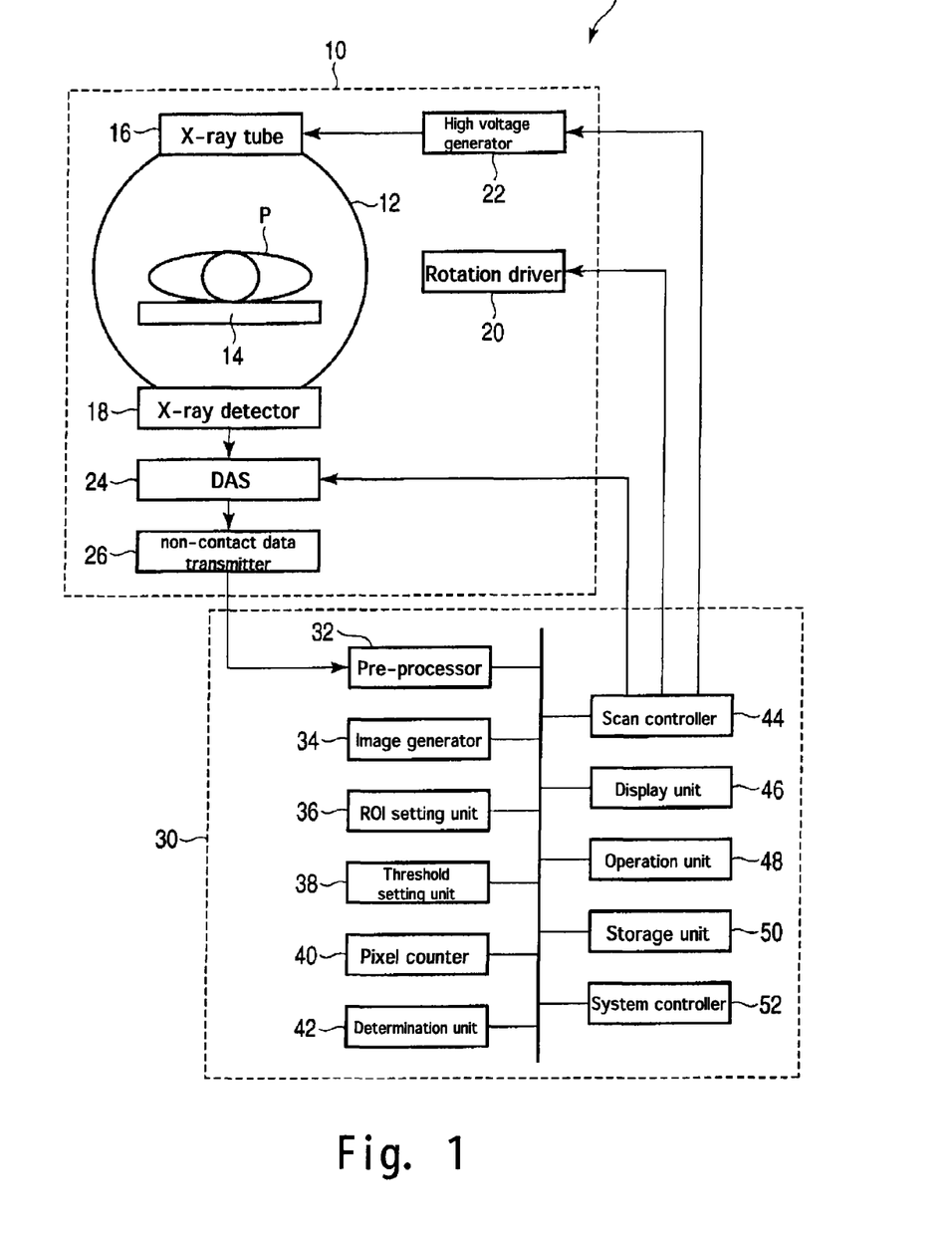
FIG. 1 is a block diagram showing components of a X-ray computed tomography imaging apparatus of a first exemplary embodiment.

FIG. 1 is a block diagram showing components of an X-ray computed tomography imaging apparatus of the first exemplary embodiment. As shown in FIG. 1, the X-ray computed tomography imaging apparatus is equipped with a scan unit (gantry) 10 and a computer 30.

The scan unit 10 has various units for X-ray scanning of a subject P. Specifically, the scan unit 10 rotatably supports rotation frame 12 having an annular or disk shape. Inside the rotation frame 12, an imaging region that the subject P on the couch 14 is inserted into is formed. The couch 14 can slide along the longitudinal direction and the vertical direction.

The rotation frame 12 includes an X-ray tube 16 and an X-ray detector 18 that are oppositely provided across the subject P on the couch 14. The rotation frame 12 receives drive signals from a rotation driver 20 and makes the X-ray tube 16 and the X-ray detector 18 rotate continuously.

The X-ray tube 16 receives a high voltage from a high voltage generator 22 and generates an X-ray. The high voltage generator 22 sends the high voltage to the X-ray tube 16 in accordance with a control signal generated by a scan controller 44 in the computer 30.

The X-ray detector 18 detects an X-ray that is generated from the X-ray tube 16 and passed through the subject P. Then the X-ray detector 18 generates an electric signal based on the intensity of the detected X-ray. A DAS (data acquisition system) 24 is connected to the X-ray detector 18.

The DAS 24 reads out a current signal from the X-ray detector 18 under control of the scan controller 44. The DAS 24 amplifies the read out current signal and converts the amplified current signal into a digital signal that forms projection data. The generated projection data is supplied to the computer 30 via a non-contact data transmitter 26.

The computer 30 includes the pre-processor 32, an image generator 34, a ROI setting unit 36, a threshold setting unit 38, a pixel counter 40, a determination unit 42, a scan controller 44, a display 46, an operation unit 48, a storage unit 50, and a system controller 52.

The pre-processor 32 executes a pre-process such as a logarithmic conversion and a sensitivity correction on the projection data supplied from the DAS 24. Such a pre-process generates projection data that is used for image reconstruction.

The image generator 34 generates data of CT images based on the pre-processed projection data. Specifically, the image generator 34 applies reconstruction processing to the projection data and reconstructs the data of CT images of the subject.

The ROI setting unit 36 sets a ROI (region of interest) for monitoring on the reconstructed CT image. The ROI is set so that the ROI includes an area subject to monitoring a degree of enhancement, such as a region of blood vessels. The ROI may be set by image processing automatically or by an input from the operation unit 48 manually. In addition, the ROI can be set not only to a certain part on the CT image, such as the blood vessel region, but also to the whole area of the CT image.

The threshold setting unit 38 sets a threshold for comparison to a number of pixels, as described in more detail below. This setting may be done based on an instruction of a user or done automatically. For example, the threshold is set based on a number of pixels instructed by direct user input via the operation unit 48, a number of pixels of a region included in the ROI designated by the user via the operation unit 48, or a number of pixels determined in accordance with the real area designated by the user via the operation unit 48. Further the threshold may be set to a predetermined value automatically.

The pixel counter 40 counts the number of pixels included in the set ROI that have a CT value in a predetermined CT value band. In other words, those pixels that are subject to the count are limited to those pixels that not only are included in the ROI, but also those pixels having a CT value in the CT value band that is subject to count.

The determination unit 42 compares the number counted by the pixel counter 40 to the threshold set by the threshold setting unit 38. Then, the determination unit 42 determines whether the counted number of pixels reaches the threshold or not. When the number of pixels does not reach the threshold, a "non-reach" signal is supplied to the scan controller 44. On the other hand, when the number of pixels reaches the threshold, a "reach" signal is supply to the scan controller 44.

The scan controller 44 controls the scan unit 10 for X-ray scanning of the subject P. When the number of pixels is below the threshold or when the non-reach signal is supplied, the scan controller 44 controls the scan unit 10 (specifically, the rotation driver 20, the high voltage generator 22, and the DAS 24) causing it to prohibit execution of predetermined action. On the other hand, when the number of pixels reaches the threshold or when the reach signal is supplied, the scan controller controls the scan unit 10 (specifically, the rotation driver 20, the high voltage generator 22, and the DAS 24) causing it to execute the predetermined action. The predetermined action is at least one of changing the scan conditions, changing from the monitoring scan to the main scan, stopping the monitoring scan, and outputting guidance, such as a respiration instruction for the subject P.

Hereinafter, three kinds of scans executed in the present embodiment are explained: a pre-scan, a monitoring scan, and a main scan. These three kinds of scans typically execute in order of a pre-scan, a monitoring scan, and a main scan. The pre-scan is executed before the injection of contrast medium into the subject P for determination of the position or size of the ROI and for setting the threshold. The monitoring scan is executed for monitoring the number of pixels included in the CT value band, which is subjected to counting. The main scan is executed for acquiring data of CT images for image diagnosis. A scan condition of the monitoring scan and a scan condition of the main scan are different. In the other words, the changing from the monitoring scan to the main scan substantially means a change of the scan conditions.

The display 48 displays CT images, the ROI used for counting, the CT value band for counting, the threshold, and the number of pixels on a display device. For example, a CRT display, a liquid crystal display, an organic EL display, a plasma display, etc. can be used as the display device.

The operation unit 48 receives information inputs and various commands from an operator. For example, the operation unit 48 receives inputs regarding the setting position of the ROI, the number of pixels, area value, etc. from the user via various input devices. A keyboard, a mouse, a switch, etc. can be used as the input device.

The storage unit 50 stores the position of the ROI, the projection data, and the data of the CT images in a non-transitory computer-readable medium, such as a hard drive, flash memory, or RAM. Furthermore, the storage unit 50 stores control programs for the X-ray computed tomography imaging apparatus 1. The control programs are executed to cause the computer 30 to control the timing of the predetermined action, in accordance with the counted number of pixels.

The system controller 52 controls the overall operation of the X-ray computed tomography imaging apparatus 1. Specifically, the system controller 52 reads out control programs stored in the storage unit 50, expands the programs in the memory, and controls various units in accordance with the expanded control programs.

Figure 2:
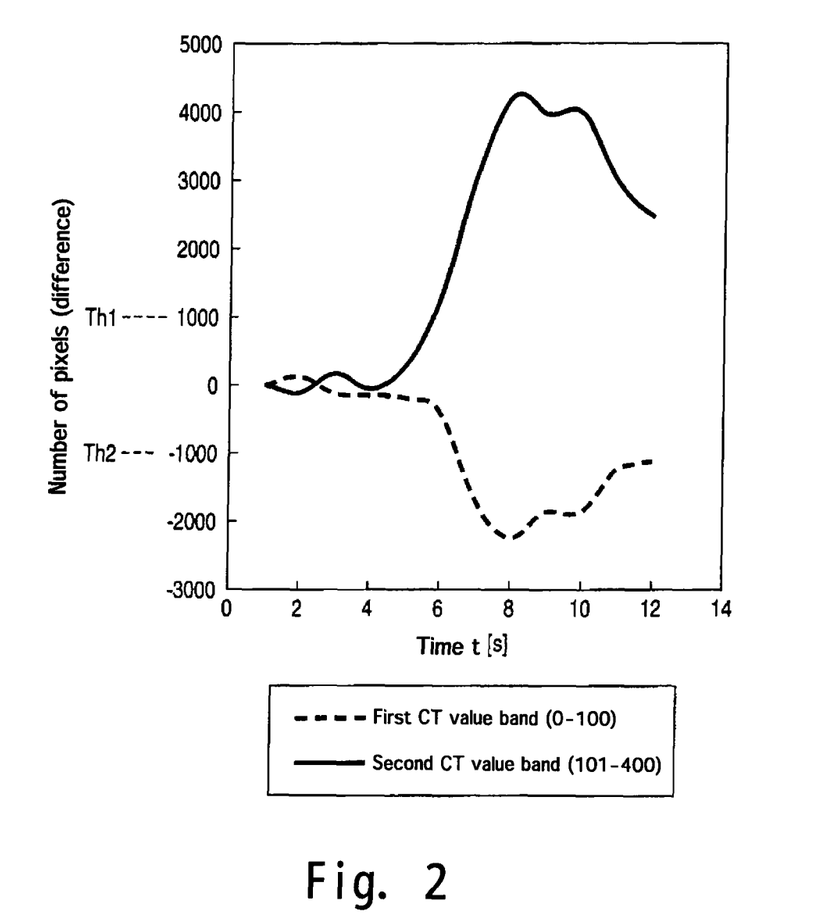
FIG. 2 is a frame format showing the time change of the number of pixels in non-enhanced and in enhanced blood vessel regions included the ROI, along with the time various of contrast medium density.

Next, a summary of the control processing of the timing of the predetermined actions is described with reference to FIG. 2. FIG. 2 is a frame format showing the time change of the number of pixels (frequency) in non-enhanced and enhanced blood vessel regions included in the ROI, along with the time variation of the contrast medium density. The vertical axis of the graph of FIG. 2 is defined as a "frequency" (number of pixels) and the horizontal axis of the graph is defined as time. The time t=1 s is the start time of the scan. The density of the contrast medium approaches its peak around time t=8 s and after that, the density decreases. The frequency of every time on the graph shows differences between a frequency at every time and a frequency at time t=0. The dashed line shows a curve indicating the time change of the frequency of pixels (non-enhanced blood vessel region) included in a first CT value band. The first CT value band is 0HU-100HU. The first CT value band corresponds to the pixels of non-enhanced blood vessels. The solid line shows a curve indicating a time change of the frequency of pixels (enhanced blood vessel region) included in a second CT value band. The second CT value band is 101HU-400HU. The second CT value band corresponds to the pixels of enhanced blood vessels.

As shown in FIG. 2, the number of pixels of the non-enhanced blood vessel region (pixel region included in CT value band 0-100) decreases and the number of pixels of the enhanced blood vessel region (pixel region included in CT value band 101-400) increases along with the increasing of the density of the contrast medium. Because the number of pixels in the CT value band is counted, the number of pixels is an index indicating the density of the contrast medium in the subject ROI.

The X-ray computed tomography imaging apparatus 1 monitors the change in the number of pixels included in the CT value band along with the density of the contrast medium, and controls the timing of the predetermined action.

For example, when the threshold Th1 (number of pixels difference) for enhanced blood vessel region is set to 1000 as shown in FIG. 2, the determination unit 42 determines in real-time whether or not the number of pixels of the enhanced blood vessel region, which is counted in real-time by the pixel counter 40, reaches the threshold value Th1. If the number of pixels is less than 1000, the scan controller 44 controls the scan unit 10 and does not execute the predetermined action. When the number of pixels transitions from less than 1000 to more than 1000, the scan controller controls the scan unit 100 and causes the predetermined action to be executed.

In addition, for example, when the threshold Th2 for the non-enhanced blood vessel region is set to −1000 as shown in FIG. 2, the determination unit 42 determines in real-time whether or not the number of pixels of the non-enhanced blood vessel region, which is counted in real-time by the pixel counter 40, reaches the threshold value Th2. If the number of pixels is higher than −1000, the scan controller 44 controls the scan unit 10 and does not execute the predetermined action. When the number of pixels transitions from more than −1000 to less than −1000, the scan controller controls the scan unit 100 and causes the predetermined action to be executed.

Next, the control of the predetermined action executed under control of the system controller 52 will be concretely described. Hereinafter, a case in which the predetermined action is the transition from the monitoring scan the main scan when the monitored subject is a heart is explained.

Before the processing of timing control, processing of condition setting for monitoring enhancement is executed. First, the condition setting will be explained. The condition setting is divided into three kinds, in accordance with the methods to set thresholds. Hereinafter, a first condition setting, a second condition setting, and a third condition setting, each of which is executed under the control of the system controller 52, are respectively explained.

Figure 3:
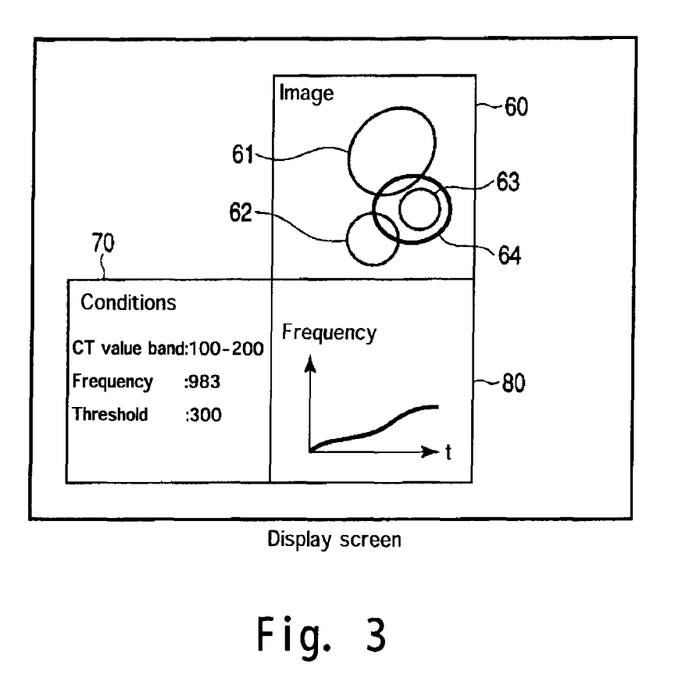
FIG. 3 is a diagram showing one example of a screen displayed on the display unit of FIG. 1 related to a first condition setting.

FIG. 3 is a diagram showing one example of a screen displayed on the display unit 46 related to the first condition setting. The display screen could be displayed not only for condition setting, but also for processing of the timing control continuously. As shown in FIG. 3, the display screen has an image display region 60, a condition display region 70, and a frequency display region 80.

In the image display region 60, a CT image generated by the pre-scan is displayed. On the CT image, the ROI that is subjected to counting of the number of pixels is superimposed and displayed. On the condition display region 70, the CT value band to be counted for the number of pixels, the number of pixels included in the CT value band, and the threshold (trigger) is displayed. On the frequency display region 80, a curve showing a time change of the number of pixels (frequency) included in the CT value band in the ROI that is subject to the count is displayed. In addition, the curve showing the time-frequency is updated on a real-time basis.

In the first condition setting, the scan controller 44 starts control of the scan unit 10 and starts the pre-scan of the chest of subject P in which contrast medium is not injected into, when the user instructs the start of the pre-scan via the operation unit 48. The pre-scan is typically done only once. The image generator 34 generates the non-enhanced image data of the chest along with execution of the pre-scan. The display unit 46 displays the generated non-enhanced image on the image display region 60. On the non-enhanced image, for example, there is a heart region 61, a spine region 62, and a descending aorta (DA) region 63, as shown in FIG. 3.

The user observes the displayed non-enhanced image and determines the region that is subject to the count (i.e., the first ROI). The user designates the first ROI 64 on the non-enhanced image via the operation unit 48. The ROI setting unit 36 identifies the coordinates of the designated first ROI 64 and stores the coordinate data of the first ROI 64 into storage unit 50. For example, when the operator wants to monitor the enhancement degree of the DA, the first ROI 64 could be set so that the first ROI 64 includes the DA region on the CT image. Herewith, the first ROI could be set to be a broader region than a monitoring part. Here, the user may not designate the first ROI, but the first ROI could be set to be the whole image.

After designation of the first ROI 64, the pixel counter 40 counts the number of pixels included in the first ROI 64 in the CT value band that is subject to the count. The CT value band that is subject to the count is set automatically or is set by the user. The CT value band that is subject to the count is set in accordance with a CT value band that could include the enhanced blood vessel (or the non-enhanced blood vessel). If the CT value band that includes the enhanced blood vessel is 101HU-400HU, the CT value band that is subject to count is set, for example, to 100HU-200HU. In this case, the pixel counter 40 counts the number of pixels included by the first ROI 64 in the CT value band 100HU-200HU. Then the display unit 46 displays the counted number of pixels on the condition display region 70. In FIG. 3, it is shown that the number of pixels (frequency) is 983 on the frequency portion of the condition display region 70.

Meanwhile, the user designates a number of pixels as the threshold (trigger) via the operation unit 48. The determination unit 42 sets the threshold in accordance with the number of pixels designated by the user. For example, as shown in FIG. 3, as the threshold, the operator designates 300 as an amount of change (relative value) from the non-enhanced blood vessel. In this case, the threshold setting unit 38 sets the threshold to 1283, which is the sum of 983 (number of pixels of non-enhanced region) and 300 (the relative value). Therefore, monitoring is executed until the number of pixels included in the first ROI in the CT value band that is subject to the count increases by 300. Further, the predetermined action is executed after the number of counted pixels increases by 300. For example, when a number of pixels of the DA region, which is the monitored part, is 600, if approximately half of the monitored region is enhanced, the determination condition is satisfied.

Here, in the first condition setting, the threshold is designated by the relative value of a number of pixels, but the first condition setting is not limited to this. For example, the threshold may be designated by a relative value with respect to any standard time, such as an injection start time. Also, the threshold value may be designated not by relative value, but by absolute value, for example, the above-mentioned 1283. In that case, the designated absolute value is set as the threshold.

Figure 4:
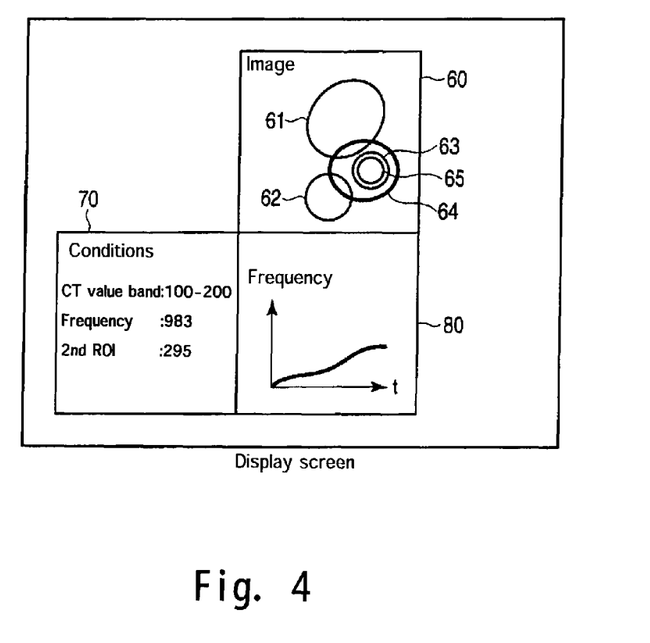
FIG. 4 is a diagram showing one example of a screen displayed on the display unit of FIG. 1 related to a second condition setting.

Next, the second condition setting is described with reference to FIG. 4. Hereinafter, an explanation of the processing that is also included in the first condition setting will be omitted. The displayed screen could be displayed not only for condition setting, but also for processing of the timing control continuously.

In the second condition setting, the user designates a second ROI 65 in addition to the first ROI. As mentioned above, the first ROI 64 is provided for limiting the area of pixels that are subjected to the count. The second ROI is designated for setting the threshold. For example, when DA region 63 in the first ROI 64 is a subject to monitoring, the user designates the second ROI 65 via the operation unit 48 so that the second ROI 65 is included in the DA region 63. The ROI setting unit 36 sets the second ROI 65 at the region designated. After the setting of the second ROI 63, the pixel counter 40 counts the pixels in the second ROI 65. Then, the threshold setting unit 38 sets the counted number of pixels in the second ROI 65 as the threshold. The display unit 46 displays the number of pixels included in the second ROI 65 on the second ROI column of the condition setting region 70. For example, as shown in FIG. 4, the number of pixels included in the second ROI 65 is 295 so that the threshold is 295. In this case, the predetermined action is started when the number of pixels included in the first ROI in the CT value band that is subject to counting to reaches 1278, which is the sum of 983 (number of pixels of non-enhanced) and 295 (the relative value).

As mentioned above, in the first condition setting, a user sets a value (number of pixels) as the threshold. However, when the user is a doctor, it is assumed that the doctor cannot convert the desired region on a CT image into a number of pixels. On the other hand, in the second condition setting, a user can designate the threshold by designating the second ROI on a CT image. Therefore, the second condition setting is a convenient way for a user to set a threshold, as compared to the first condition setting method.

Figure 5:
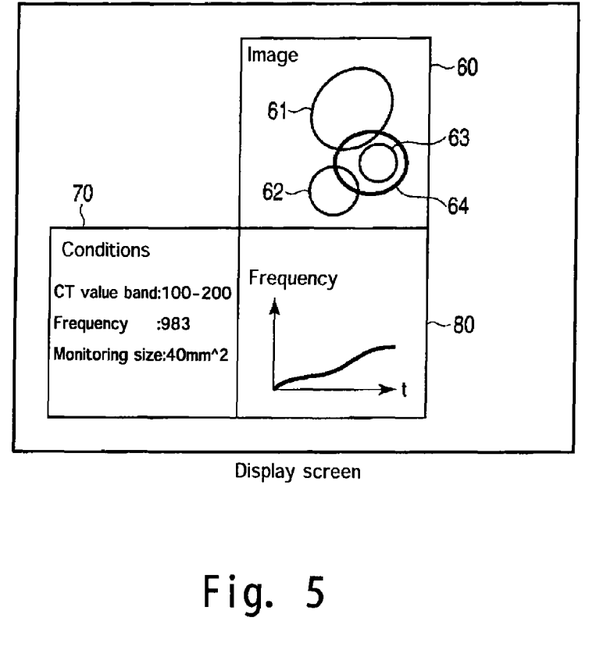
FIG. 5 is a diagram showing one example of a screen displayed on the display unit of FIG. 1 related to a third condition setting.

Next, the third condition setting is explained with reference to FIG. 5. Hereinafter, the explanation of the processing that is also included in the first condition setting will be omitted. The displayed screen could be displayed not only for condition setting, but also for processing of the timing control continuously.

In the third condition setting, a user inputs an area value (e.g., in mm^2) of real space for setting a threshold. When the user inputs the area value via the operation unit 48, the threshold setting unit 38 calculates a number of pixels corresponding to the area value based on the area value and an enlargement factor of the CT image. For example, if the user inputs the value 40 mm^2 as an area value of the monitoring part, the threshold setting unit 38 calculates the number of pixels corresponding to 40 mm^2, and sets the calculated number of pixels as the threshold. As shown in FIG. 5, the inputted value 40 mm^2 is displayed in the condition setting region 70.

In addition, in this third condition setting, the user inputs an area value for setting the threshold. However, the third condition setting is not limited to that. For example, the user may input a value related to a diameter or radius instead of an area value for setting the threshold. In that case, the threshold setting unit 38 calculates a number of pixels corresponding to the inputted value based on the area value and an enlargement factor of the CT image, and sets the calculated number of pixels as the threshold. If the blood vessel that is subject to be monitored is a relatively large blood vessel, diameters are often used to indicate size. If blood vessels that are subjected to be monitored are widely distributed, a sum of regions of the blood vessels could be used to indicate size.

As mentioned above, in the first condition setting, a user sets a value (number of pixels) as the threshold. However, when the user is a doctor, it is assumed that the doctor cannot convert the desired region on a CT image into number of pixels. On the other hand, in the third condition setting, a user can designate the threshold by designating an area value. It is assumed that the area value in real space is more familiar than the number of pixels for a general user. Therefore, the second condition setting is a convenient method for a user to set a threshold, as compared to the first condition setting.

Here, the explanation of condition setting is completed. Note that the kind of condition settings or the method used to set the threshold can be selected by the user.

Figure 6:
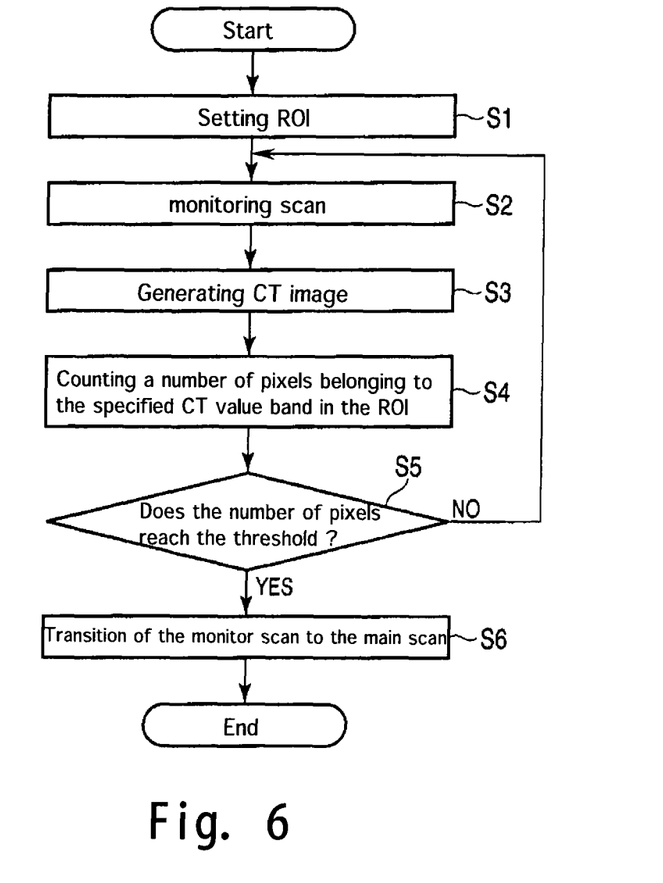
FIG. 6 is a flowchart showing a typical process of a transition timing control executed by the controller.

Next, transition timing control from the monitoring scan to the main scan will be explained. The transition timing control is executed based on the threshold set by the above-mentioned condition setting. FIG. 6 is a flowchart showing a process of the transition timing control executed by the system controller 52. This transition timing control is the same regardless of the type of condition setting described above.

First, the system controller 52 causes the ROI setting unit 36 to process the setting of the ROI (step S1). In step S1, the ROI setting unit 36 sets the first ROI that is subjected to the count on a CT image in accordance with the first condition setting, the second condition setting, or the third condition setting. The size and position of the first ROI is set on the CT image generated by the pre-scan. The coordinate data on a CT image of the first ROI is stored in the storage unit 50.

When step S1 is performed, the system controller 52 waits for a start order of the monitoring scan from the operation unit 48. If the start of the monitoring scan is ready, a user may input the start order of the monitoring scan via the operation unit 48. Here, it does not matter whether the contrast medium is injected after the start order or before the start order.

After the start order, the system controller 52 causes the scan controller 44 to start a monitoring scan (step S2). In step S2, the scan controller 44 controls the scan unit 10 and performs a monitoring scan. The scan region of the monitoring scan may be the same as the scan region of the pre-scan. Because the monitoring scan is performed for monitoring a degree of enhancement, the condition of the monitoring scan is of relatively lower quality. For example, in the monitoring scan, the scan is repeated not continuously, but intermittently, for example, at one second intervals. The tube current value is also weaker than that of the main scan. On the basis of such scan conditions of the monitoring scan, the scan controller controls the high voltage generator 22 and makes the X-ray tube 16 generates X-ray. The X-ray detector 18 detects an X-ray passed through the subject P and generates a current signal. The DAS 24 reads out the current signal from the X-ray detector in accordance under control of the scan controller 44. Projection data is generated from the read-out current signal.

After performing step S2, the system controller 52 causes the image generator 34 to execute the process of image generation (Step S3). In step S3, the image generator 34 generates data of a CT image regarding a slice that is subjected to the scan, based on projection data for one slice acquired in step S2. The display unit 46 displays the generated CT image on the image display region 60 on the display screen shown in FIG. 3.

After performing step S3, the system controller 52 causes the pixel counter 40 to execute a counting process (step S4). In step S4, the pixel counter 40 reads-out the coordinate data of the first ROI set in step S1 from the storage unit 50. Then, the ROI setting unit 36 automatically sets the first ROI at the read-out coordinates on the CT image generated by the monitoring scan at step S3. The display unit 46 displays the set first ROI on the CT image.

Next, the pixel counter 40 generates a histogram of pixel values for the set first ROI. Then the pixel counter 40 counts the number of pixels included in the CT value band that are subject to the count using the histogram. When the number of pixels is counted, the display unit 46 updates the curve indicating the time change of the number of pixels on the frequency display region 70 shown in FIG. 3.

After performing step S4, the system controller 52 causes the determination unit 42 to execute determination processing (step S5). In step S5, the determination unit 42 determines whether or not the number of pixels counted in step S4 reaches the predetermined threshold.

When the number of pixels does not reach the threshold (No in step S5), the system controller supplies a "non-reach" signal to the scan controller 44. When the "non-reach" signal is supplied, the scan controller 44 continues performing the monitoring scan based on the conditions set for the monitoring scan. Steps S2 to S5 are repeated again. Herewith, steps S2-S5 are repeated until the time the number of pixels reaches the predetermined threshold.

On the other hand, when the number of pixels reaches the threshold (Yes in step S5), the system controller 52 supplies a "reach" signal to the scan controller 44. When the "reach" signal is supplied, the scan controller 44 causes the scan unit 10 to transition from the monitoring scan to the main scan (step S6). Specifically, the scan controller, at first, stops the monitoring scan. Next, the scan controller changes a scan condition from the scan condition of the monitoring scan to the scan condition of the main scan, and a scan is performed in accordance with the changed scan condition. The scan condition includes at least one of a number of detector rows used for the scan, a tube current value, a tube voltage value, an X-ray irradiation time, an X-ray generation interval, and an imaging mode (helical scan, conventional scan, etc.).

For example, along with the transition from the monitoring scan to the main scan, increasing the number of detector rows or changing the tube current value or the tube voltage value can be performed. Shortening of the X-ray irradiation time, lengthening the X-ray generation interval, or changing from a conventional scan to a helical scan also could be executed at this time.

In addition, the predetermined action executed when the number of the pixels reaches the threshold is not limited to changing the scan condition. For example, the predetermined action does not have to be a transition to the main scan, but could be just stopping the scan. Furthermore, when the number of pixels reaches the threshold, guidance for respiration can be outputted. An example of the operation in this case is explained below.

Because the monitoring scan is performed for a relatively long time, the subject P is often allowed to breathe freely. On the other hand, because the main scan is performed for a relatively short time, before the start of the main scan, respiration guidance instructing the subject to hold his or her breath is performed. Typically, the respiration guidance is performed after the monitoring scan. For example, the guidance is performed by output of sound data, such as: "Please hold breath."

In this case, when the number of pixels reaches the threshold at step S5, the scan controller 44 reads out sound data stored in the storage unit 50. Then, the scan controller 44 outputs the sound data by a speaker provided on the scan unit 10, for example. The guidance of respiration is performed in this manner.

Furthermore, the predetermined action is not limited to only one action. For example, when the number of pixels reaches the threshold, the transition from the monitoring scan to the main scan and the output of the guidance can be performed successively.

After performing step S6, the system controller 52 terminates the timing control of the predetermined action.

According to the above-mentioned timing control of the predetermined action, the X-ray computed tomography imaging apparatus monitors an enhancement degree of a part of the subject that is subject to monitoring by monitoring the number of pixels included in the CT value band that is subject to the count. Hereinafter, the effects of the timing control of the predetermined action of the present embodiment are described.

Conventionally, enhancement degree was monitored in accordance with an average CT value in the first ROI. In this manner, the part subject to monitoring could shift due to body motion or respiration of the subject P and a high CT value region, such as the spine area, could became part of the first ROI. In this case, accurate diagnosis was difficult.

However, according to the present embodiment, the number of pixels in the first ROI is counted and the CT value that is subject to count is limited to a certain band, for example, the CT value of an enhanced blood vessel, which is lower than the CT value of the spine area. By limiting the CT value band that is subject to the count, the X-ray computed tomography imaging apparatus 1 of the present embodiment can eliminate pixels in high CT value areas from being subject to the count, even if a high CT value area becomes part of the first ROI. Therefore, the X-ray computed tomography imaging apparatus 1 can more accurately monitor the enhancement degree in comparison with a system that monitors the average CT value.

Next, there is the case in which the monitored part is a part that cannot be specified on the non-enhanced image, such as the carotid artery. In that case, only an approximate position is known and a broad first ROI is set. In the case of monitoring the average CT value, when the broader first ROI is set, many parts other than the part that is subject to monitoring are included in the first ROI. Therefore, the contribution rate of the CT value of the monitored part to the average CT value of the first ROI is lower and the accuracy of monitoring enhancement is worse.

However, the X-ray computed tomography imaging apparatus 1 of the present embodiment monitors the enhancement in accordance with the number of the pixels belonging to a CT value band that is subjected to the count. Thus, even if the first ROI is set broader, parts other than the part that is subject to monitoring are automatically eliminated based on their CT value. Therefore, the X-ray computed tomography imaging apparatus 1 of the present embodiment can work with a broader first ROI than that of a conventionally known apparatus.

Figure 7:
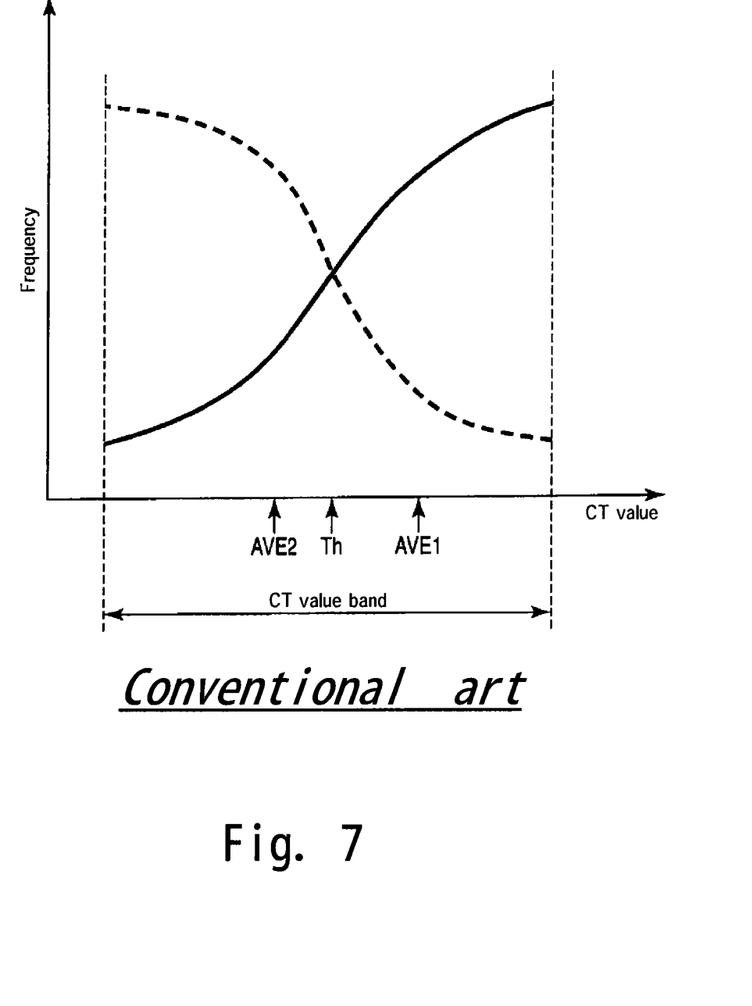
FIG. 7 is a graph for explaining problems of the background art in accordance with monitoring an average CT value.

Next, the case in which the subject of calculating an average value is limited to pixels included in a specified CT value band in the first ROI is discussed. For example, as shown in FIG. 7, two frequency distribution curves respectively correspond to a same number of pixels in the the specified CT value band. In this case, AVE1 (average CT value of frequency distribution curve shown as solid line) is higher than the AVE2 (average CT value of frequency distribution curve shown as dashed line). For example, when the threshold Th is set between AVE1 and AVE2, the frequency distribution curve shown as a solid line satisfies the condition, but the frequency distribution curve shown as dashed line does not satisfied the condition. Herewith, if the monitoring is performed based on the average CT value, the monitoring result is severely affected by the threshold. However, when monitoring is performed based on the number of pixels, as in the present embodiment, the result of monitoring is not affected by the frequency distribution within the specific CT value band. Therefore, the X-ray computed tomography imaging apparatus 1 has improved accuracy of monitoring, in comparison with the conventionally known apparatus.

As mentioned above, according to the present embodiment, the accuracy of monitoring enhancement is improved.

In addition, in the above mentioned description, only one CT value band is subjected to the count. However, the present embodiment is not limited to this. For example, the CT value band that is subject to the count could include a plurality of CT value bands. In this case, the threshold setting unit 38 sets thresholds for each of the CT value bands. The pixel counter 40 counts a plurality of numbers of pixels, each of which belongs to different CT value bands, respectively. The determination unit 42 determines whether or not the number of pixels for respective CT value bands reach the corresponding thresholds. Then, the scan controller 44 controls the timing of a predetermined action in accordance with a plurality of results of the determinations for the CT value bands. For example, the scan controller 44 may cause the predetermined action to be performed when each of the number of pixels reaches a corresponding threshold. Alternatively, the scan controller 44 may cause the predetermined action to be performed when one of the numbers of pixels reaches a corresponding threshold.

Here, with regard to the first embodiment, the ROI setting unit 36, the threshold setting unit 138, the pixel counter 40, and the determination unit 42 can correspond to means for monitoring. Further, each of the above units can be implemented as a hardware circuit or as a hardware/software combination, e.g., as a processor executing a corresponding software program.

Figure 8:
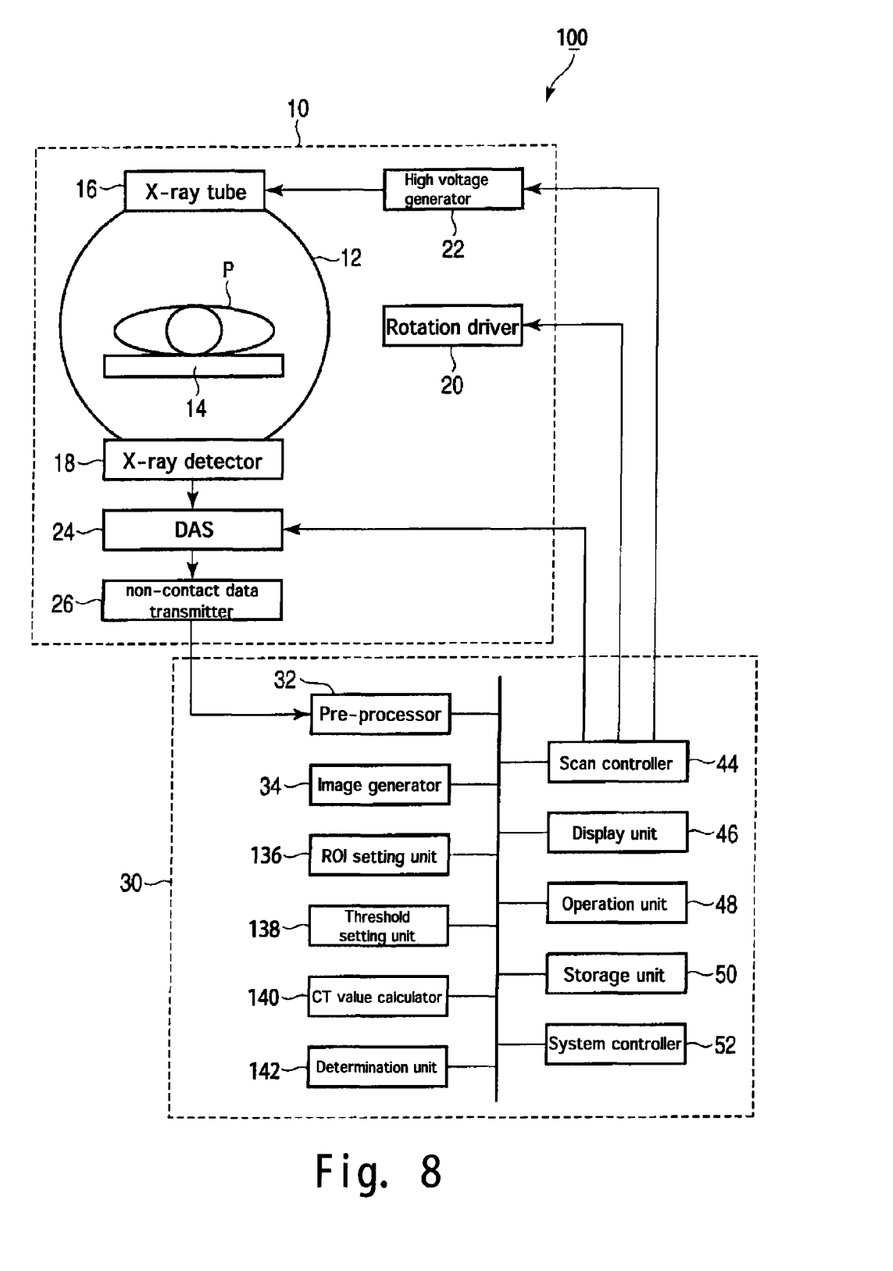
FIG. 8 is a block diagram showing components of a X-ray computed tomography imaging apparatus of a second exemplary embodiment.

In the first embodiment, the monitoring is performed in accordance with the number of pixels belonging to a CT value band that is subject to the count. On the other hand, in the second embodiment, a sub-ROI is set in the first ROI and the area to be monitored is specified in accordance with a selection of the sub-ROI. Here, for similar components and operations included in the first embodiment, no further explanation is provided. The same reference symbols are used for the same components, while different symbols are used for different components with respect to the first embodiment. FIG. 8 is a block diagram showing components of a X-ray computed tomography imaging apparatus 100 of the second embodiment.

Figure 9:
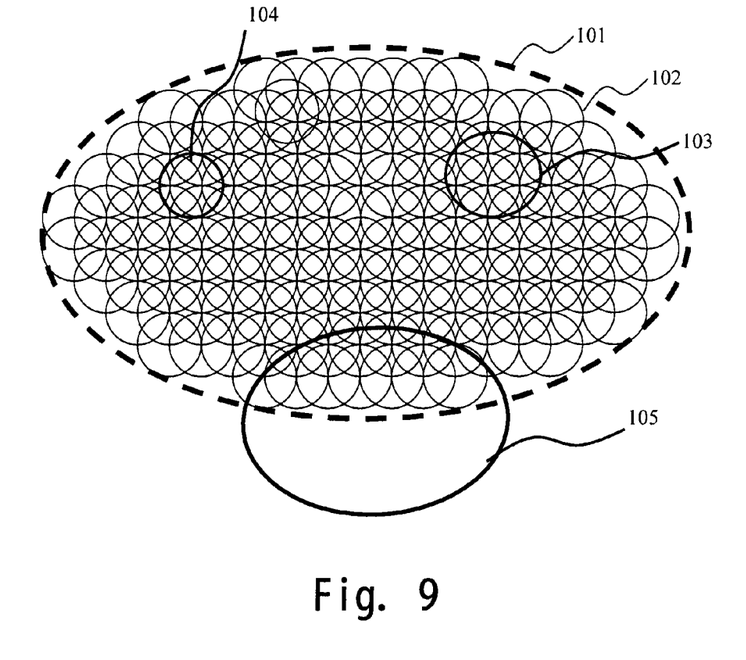
FIG. 9 is a frame format showing position relation between ROI and sub-ROIs set by the ROI setting unit of FIG. 8.

In the present embodiment, an ROI setting unit 136 sets the first ROI 101 for monitoring, as in the first embodiment. Furthermore, the ROI setting unit 136 sets a plurality of sub-ROIs 102 within the first ROI 101. In FIG. 9, the relationship between the first ROI 101 and the sub ROIs 102 is shown. In FIG. 9, a case in which the carotid artery is monitored is shown as one example. As shown in FIG. 9, a calcification area 104 and a spine area may be included in the first ROI 101. The sub-ROIs are set so that the first ROI 101 is filled. Here, in FIG. 9, a case in which no sub-ROI protrudes from the first ROI 101 is shown, but the present embodiment is not limited to this. As a result of setting the sub-ROIs so that any region of the first ROI 101 is covered by a sub-ROI 102, a part of the sub-ROIs may protrude from the area of the first ROI 101.

Regarding a size of one of the sub-ROIs, because the size of a subject part, such as a diameter of a blood vessel, can vary depending on what the subject part is or the field of view, the size of the sub-ROIs can be changed according to the subject part. In addition, in FIG. 9, the distance between neighboring sub-ROIs 102 is one-half of the diameter of the sub-ROIs 102, but the present embodiment is not limited to this. Having denser sub-ROIs leads to better performance, but with a higher processing cost, while having coarser sub-ROIs results in faster processing, but less accurate performance. Here, it is preferable that the distance between neighboring sub-ROIs 102 is 1/n (n being 2 or larger) of the diameter of the sub-ROIs 102, because the sub-ROIs 102 cover the first ROI 101 efficiently.

Figure 10:
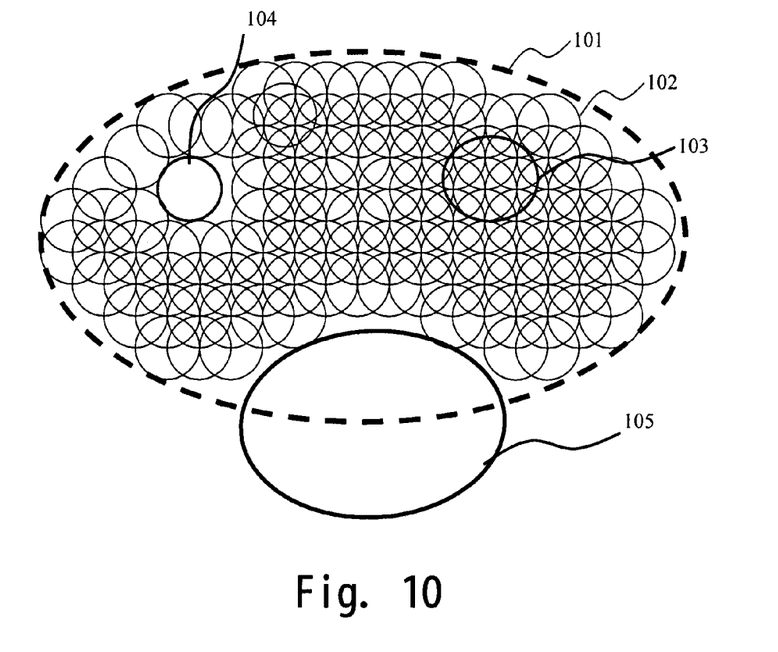
FIG. 10 is a frame format showing the selection of sub-ROIs by the ROI setting unit of FIG. 8.

Next, the ROI setting unit 136 measures the CT value in each sub-ROI 102, respectively, and selects sub-ROIs having CT values belonging to the CT value band to be monitored. Specifically, a calcification area 104, a spine area 105, and an air area are not monitored. A calcification area and a spine area have a high CT value and an air area has low CT value.

In this embodiment, the method used to select the sub-ROIs can be different. One example is explained as follows. First, an area value having a higher CT value than a specified value corresponding to bones or calcification is calculated. Next, the number of sub-ROIs that should be eliminated in accordance with the area value is calculated. Then the calculated number of sub-ROIs are eliminated from being monitored in the order of CT value starting from the highest. The method used to select the sub-ROIs mentioned above can be changed in accordance with the subject part to be monitored.

In the present embodiment, because a bone or calcification area is eliminated by selecting sub-ROIs, the timing control of the predetermined action is determined in a different manner from the first embodiment.

First, the threshold setting unit 138 sets the threshold for comparison to the CT value of selected sub-ROIs manually or automatically.

For each CT image, the CT value calculation unit 140 calculates the average of CT values of three sub-ROIs out of the sub-ROIs that are not eliminated by the above-mentioned selection of sub-ROIs, the three sub-ROIs being selected in the order of CT value starting from the highest. Alternatively, the CT value calculation unit 140 sums the CT values of the three sub-ROIs out of the sub-ROIs that are not eliminated by the above-mentioned selection of sub-ROIs to generate an index.

Meanwhile, the CT value calculation unit 140 displays a position of the sub-ROI having the highest CT value on the screen of the display unit 46. Here, the number of sub-ROIs that are subjected to calculation is not limited to three. The number could be one or more and the number can be changed along with the size or spacing interval of the sub-ROIs. It is preferable that the number is set so that a peculiar CT value caused by noise can be absorbed and the regional change of CT value caused by the contrast medium is not hidden. Furthermore, the sub-ROI whose position is displayed on the screen is not limited to only one. Positions of all or less than all of the sub-ROIs that are subjected to calculation can be displayed.

The determination unit 142 compares the average CT value calculated by the CT value calculation unit 140 to the threshold set by the threshold setting unit 138. The determination unit 142 determines whether or not the calculated average CT value reaches the threshold. When the average CT value does not reach the threshold, a "non-reach" signal is supplied to the scan controller 44. On the other hand, when the average CT value reaches the threshold, a "reach" signal is supplied to the scan controller 44. Alternatively, the determination unit 142 compares the calculated index (sum of CT values) to a corresponding index threshold.

The threshold setting unit 138, the CT value calculation unit 140, and the determination unit 142 may be replaced by the threshold value setting unit 38, the pixel counter 40, and the determination unit 42. In this case, for the sub-ROI areas not eliminated by the above-mentioned process, the system is configured to execute the operation in the same way as in the first embodiment, i.e., the system is configured to count the pixels falling within the specified pixel value band among the pixels in all of the sub-ROIs not eliminated.

Furthermore, the scan controller 44 may be configured to operate in the same way as in the first embodiment, but may be configured to execute the transition to the main scan after waiting for the input order from an operator. When the position of a sub-ROI having the highest CT value is displayed on the screen, as mentioned above, the operator can confirm whether or not the position of the sub-ROI is really suitable to monitor. Therefore, in the present embodiment, the scan controller 44 may perform a display for prompting input from the operator for transition to the main scan after receiving the reach signal, which means the average CT value reached the threshold. In this case, the scan controller waits for the input of the operator and executes transition to the main scan. In this way, the operator can perform the main scan upon confirmation of whether or not there is a CT value increasing, which indicates that it is proper to perform the predetermined action.

According to the present embodiment, the X-ray computed tomography imaging apparatus 100 monitors enhancement of the selected sub-ROI 102. Hereinafter, the effect of controlling the timing of the predetermined action of the present embodiment is explained.

Conventionally, enhancement was monitored in accordance with an average CT value in the first ROI. In this manner, the part that is subject to monitoring could shift due to body motion or respiration of the subject P and a high CT value region, such as the spine area, could be mixed in the first ROI. In this case, accurate diagnosis was difficult.

However, according to the present embodiment, the sub-ROIs are set in the first ROI and the monitored sub-ROIs are those remaining sub-ROIs after eliminating sub-ROIs corresponding a spine region, etc. based on a CT value band. Therefore, the CT value band that is subjected to monitoring is limited to a specified band, for example, a CT value band corresponding to an enhanced blood vessel area, which has a lower CT value than that of the spine area. By limiting the sub-ROIs that are subject to monitoring, the X-ray computed tomography imaging apparatus 100 of the present embodiment can eliminate a high CT value area from being subject to monitoring, even if the high CT value area is mixed in the first ROI. Therefore the X-ray computed tomography imaging apparatus 100 can more effectively monitor enhancement, as compared with the conventional method in which the average CT value of the entire region is monitored.

Next, there is the case in which the monitoring part is a part that cannot be specified on the non-enhanced image, such as the carotid artery. In that case, because only an approximate position can be identified, a broader first ROI must be set. In the case of monitoring the average CT value, when a broader first ROI is set, many parts other than the part that is subject to monitoring are included in the first ROI. Therefore, the contribution rate of CT value of the monitoring part to the average CT value of the first ROI is decreased and the accuracy of the monitoring enhancement is lower.

However, the X-ray computed tomography imaging apparatus 100 of the present embodiment monitors the enhancement in accordance with the sub-ROIs belonging to the CT value band that is subjected to monitoring. Here, even if the first ROI is set broader, parts other than the part that is subject to monitoring can be automatically eliminated based on CT value. Therefore, the X-ray computed tomography imaging apparatus 100 of the present embodiment can set a broader first ROI than that of a conventionally known apparatus.

As mentioned above, according to the present embodiment, the accuracy of monitoring enhancement is advanced.

Here, with regard to the second embodiment, the ROI setting unit 136, the threshold setting unit 138, the CT value calculation unit 140, and the determination unit 142 can correspond to the means for monitoring. Each of the described units can be implemented as a hardware circuit or as a hardware/software combination e.g., as a process executing a corresponding software program.

While certain embodiments have been described, these embodiments have been presented by way of example only, and are not intended to limit the scope of the inventions. Indeed, the novel methods and systems described herein may be embodied in a variety of other forms. Furthermore, various omissions, substitutions, and changes in the form of the methods and systems described herein may be made without departing from the sprit of the inventions. The accompanying claims and their equivalents are intended to cover such forms or modifications as would fall within the scope and spirit of the inventions.

What is claimed is:

1. An image diagnostic apparatus, comprising:
    a scan unit configured to repeatedly scan a subject and to repeatedly acquire acquisition data related to the subject;
    a generation unit configured to generate medical images related to the subject based on the acquired acquisition data;
    a monitoring unit configured to monitor a change in the medical images based on a specified pixel value band, which has a predetermined upper limit and a predetermined lower limit, wherein the monitoring unit includes a counter configured to count a number of pixels included in the specified pixel value band in each of the medical images;
    a controller configured to control timing of a predetermined action of the scan unit based on the change in the medical images monitored by the monitoring unit, wherein the predetermined action of the scan unit is at least one of changing a scan condition, stopping a scan, and outputting guidance to the subject.

2. The image diagnostic apparatus of claim 1, wherein the monitoring unit further comprises:
- a determination unit configured to determine whether or not the counted number of pixels reaches a predetermined threshold,
- wherein the controller is further configured to prohibit execution of the predetermined action when the counted number of pixels does not reach the predetermined threshold, and to cause the predetermined action to be executed when the counted number of pixels reaches the predetermined threshold.

3. The image diagnostic apparatus of claim 1, wherein the scan condition is at least one of a number of detector rows, a tube current value, a tube voltage value, an X-ray irradiation time, an X-ray generation interval, and an imaging mode.

4. The image diagnostic apparatus of claim 1, wherein the predetermined threshold is set as one of a number directly designated by a user, a number of pixels corresponding to an area value designated by the user, and a number of pixels included in an ROI on the medical image set by the user.

5. The image diagnostic apparatus of claim 2, wherein the determination unit is further configured
- to determine that the counted number of pixels does not reach the predetermined threshold when the counted number of pixels remains above or below the predetermined threshold, and
- to determine that the counted number of pixels reaches the predetermined threshold when the counted number of pixels transitions from a number lower than the predetermined threshold to a number higher than the predetermined threshold, or when the counted number of pixels transitions from the number higher than the predetermined threshold to the number lower than the predetermined threshold.

6. The image diagnostic apparatus of claim 2, further comprising;
- an ROI setting unit configured to set an ROI on an entire area or on a specified area of the medical images automatically, or based on an instruction of a user,
- wherein the counter is further configured to count the number of pixels in the specified pixel value band within the ROI.

7. The image diagnostic apparatus of claim 1, wherein the monitoring unit further comprises:
- an ROI setting unit configured to set a plurality of sub-ROIs on the medical images, and to eliminate at least one of the plurality of sub-ROIs from being monitored when the eliminated at least one sub-ROI does not have any pixel values in the specified pixel value band.

8. The image diagnostic apparatus of claim 7, wherein the ROI setting unit is further configured to set a first ROI on the medical images, and to set the plurality of sub-ROIs so that the first ROI is substantially covered by the plurality of sub-ROIs.

9. The image diagnostic apparatus of claim 7, wherein the monitoring unit further comprises:
- a calculator configured to calculate an index by adding a plurality of pixel values in a selected subset of sub-ROIs selected from the plurality sub-ROIs; and
- a determination unit configured to determine whether or not the index reaches a predetermined threshold,
- wherein the controller is further configured to prohibit execution of the predetermined action when the index does not reach the predetermined threshold, and to cause the predetermined action to be executed when the index reaches the predetermined threshold.

10. The image diagnostic apparatus of claim 9, wherein
- the calculator is further configured to cause at least one of the sub-ROIs that is subjected to calculation of the index to be displayed on the medical images; and
- the controller is further configured to cause the predetermined action to be performed after an input from a user.

11. An image diagnostic method, comprising;
- scanning a subject repeatedly using a scan unit to acquire acquisition data related to the subject;
- generating medical images related to the subject based on the acquired acquisition data;
- monitoring a change in the medical images based on a specified pixel value band, which has a predetermined upper limit and a predetermined lower limit, wherein the monitoring step includes counting a number of pixels included in the specified pixel value band in each of the medical images;
- controlling timing of a predetermined action of the scan unit based on the change in the medical images monitored in the monitoring step, wherein the predetermined action of the scan unit is at least one of changing a scan condition, stopping a scan, and outputting guidance to the subject.

12. The image diagnostic method of claim 11, wherein the monitoring step further comprises:
- determining whether or not the counted number of pixels reaches a predetermined threshold,
- wherein the controlling step further comprises prohibiting execution of the predetermined action when the counted number of pixels does not reach the predetermined threshold, and to cause the predetermined action to be executed when the counted number of pixels reaches the predetermined threshold.

13. The image diagnostic method of claim 11, wherein the scan condition is at least one of a number of detector rows, a tube current value, a tube voltage value, an X-ray irradiation time, an X-ray generation interval, and an imaging mode.

14. The image diagnostic method of claim 11, wherein the predetermined threshold is set as one of a number directly designated by a user, a number of pixels corresponding to an area value designated by the user, and a number of pixels included in a ROI on the medical image set by the user.

15. The image diagnostic method of claim 12, wherein the determining step further comprises:
- determining that the counted number of pixels does not reach the predetermined threshold when the counted number of pixels remains above or below the predetermined threshold, and
- determining that the counted number of pixels reaches the predetermined threshold when the counted number of pixels transitions from a number lower than the predetermined threshold to a number higher than the predetermined threshold, or when the counted number of pixels transitions from the number higher than the predetermined threshold to the number lower than the predetermined threshold.

16. The image diagnostic method of claim 12, further comprising:
- setting an ROI on an entire area or a specified area of the medical images automatically, or based on an instruction of a user,
- wherein the counting step further comprises counting the number of pixels in the specified pixel value band within the ROI.

17. The image diagnostic method of claim 11, wherein the monitoring step further comprises:
- setting a plurality of sub-ROIs on the medical images; and
- eliminating at least one of the plurality of sub-ROIs from being monitored when the at least one sub-ROI does not have any pixel values in the specified pixel value band.

18. The image diagnostic method of claim 17, wherein the setting step comprises:
- setting a first ROI on the medical images; and
- setting the plurality of sub-ROIs so that the first ROI is substantially covered by the plurality of sub-ROIs.

19. The image diagnostic method according to claim 17, wherein the monitoring step further comprises:
- calculating an index by adding a plurality of pixel values in a selected subset of sub-ROIs selected from the plurality sub-ROIs;
- determining whether or not the index reaches a predetermined threshold;
- prohibiting execution of the predetermined action when the index does not reach the predetermined threshold;
- and causing the predetermined action to be executed when the index reaches the predetermined threshold.

20. The image diagnostic apparatus according to claim 19, wherein the calculating step further comprises:
- causing at least one of the sub-ROIs that is subjected to calculation of the index to be displayed on the medical images; and
- causing the predetermined action to be performed after an input from a user.

21. An image diagnostic apparatus, comprising:
- a scan unit configured to repeatedly scan a subject and to repeatedly acquire acquisition data related to the subject;
- a generation unit configured to generate medical images related to the subject based on the acquired acquisition data;
- means for monitoring a change in the medical images based on a specified pixel value band, which has a predetermined upper limit and a predetermined lower limit, wherein the means for monitoring includes means for counting a number of pixels included in the specified pixel value band in each of the medical images;
- a controller unit configured to control timing of a predetermined action of the scan unit based on the change in the medical images monitored by the means for monitoring, wherein the predetermined action of the scan unit is at least one of changing a scan condition, stopping a scan, and outputting guidance to the subject.

22. A non-transitory computer readable medium storing a program that, when executed by a computer, causes the computer to execute the steps of:
- scanning a subject repeatedly using a scan unit to acquire acquisition data related to the subject;
- generating medical images related to the subject based on the acquired acquisition data;
- monitoring a change in the medical images based on a specified pixel value band, which has a predetermined upper limit and a predetermined lower limit, wherein the monitoring step includes counting a number of pixels included in the specified pixel value band in each of the medical images;
- controlling timing of a predetermined action of the scan unit based on the change in the medical images monitored in the monitoring step, wherein the predetermined action of the scan unit is at least one of changing a scan condition, stopping a scan, and outputting guidance to the subject.

* * * * *